(12) United States Patent
Kasai et al.

(10) Patent No.: US 8,454,942 B1
(45) Date of Patent: Jun. 4, 2013

(54) COSMETIC OIL MOUSSE COMPOSITION

(75) Inventors: Takehiko Kasai, Kawasaki (JP);
Anthony Potin, Hoboken, NJ (US);
Philippe Touzan, Paris (FR); Paula Cziryak, Eatontown, NJ (US); Ana Kljuic, New York, NY (US)

(73) Assignee: L'Oreal, Paris (FR)

( * ) Notice: Subject to any disclaimer, the term of this patent is extended or adjusted under 35 U.S.C. 154(b) by 30 days.

(21) Appl. No.: 13/305,841

(22) Filed: Nov. 29, 2011

(51) Int. Cl.
*A61K 8/00* (2006.01)
*A61K 8/18* (2006.01)
*A61Q 17/04* (2006.01)

(52) U.S. Cl.
USPC .......................................................... 424/59

(58) Field of Classification Search
USPC .......................................................... 424/59
See application file for complete search history.

(56) References Cited

U.S. PATENT DOCUMENTS

| | | | |
|---|---|---|---|
| 2,463,264 | A | 3/1949 | Graenacher et al. |
| 5,166,355 | A | 11/1992 | Leistner et al. |
| 5,237,071 | A | 8/1993 | Leistner et al. |
| 2004/0197276 | A1 | 10/2004 | Takase et al. |
| 2005/0287081 | A1 | 12/2005 | Aust et al. |
| 2010/0111884 | A1 * | 5/2010 | Acker et al. ................ 424/60 |

FOREIGN PATENT DOCUMENTS

| | | |
|---|---|---|
| DE | 19726184 | 12/1998 |
| DE | 19746654 | 2/1999 |
| DE | 19755649 | 6/1999 |
| DE | 19855649 | 6/2000 |
| DE | 10162844 | 7/2003 |
| EP | 133981 | 3/1985 |
| EP | 669323 | 8/1995 |
| EP | 0832642 | 4/1998 |
| EP | 893119 | 1/1999 |
| EP | 0967200 | 12/1999 |
| EP | 1008586 A1 | 6/2000 |
| EP | 1027883 | 8/2000 |
| EP | 1133980 | 9/2001 |
| EP | 1300137 | 4/2003 |
| GB | 2206339 | 1/1989 |
| GB | 2303549 | 2/1997 |
| WO | WO 93/04665 | 3/1993 |
| WO | WO 2010/041141 A2 | 4/2010 |

OTHER PUBLICATIONS

Cosmetics & Toiletries, Feb. 1990, vol. 105, p. 53-64.

* cited by examiner

*Primary Examiner* — Daniel Sullivan
*Assistant Examiner* — Trevor Love
(74) *Attorney, Agent, or Firm* — L'Oreal USA

(57) ABSTRACT

An anhydrous oil foam composition containing: (a) at least one liquid oil; (b) at least one surfactant chosen from polyglyceryl-2 laurate; (c) at least one UV filter; and (d) a propellant, wherein the composition is waterless and is capable of imparting UV protection onto a target keratinous substrate.

9 Claims, No Drawings

COSMETIC OIL MOUSSE COMPOSITION

BACKGROUND OF THE INVENTION

The present invention generally relates to oil foam compositions capable of imparting UV protection. More particularly, the present invention relates to a waterless, or substantially waterless, oil foam composition, preferably in the form of an oil mousse, for application onto a keratinous substrate such as hair, skin or nails for UV protection.

Foams are complex dispersion systems which do not form under all circumstances. It is known to be very difficult to produce foams which are homogenous, stable, and breakable upon application of mechanical force and which can provide a shelf-stable composition. One of the primary disadvantages associated with the use of foams is their foam stability. In order for the foam to perform satisfactorily, the actives finely dispersed therein must be satisfactorily distributed over the target surface. This in turn requires that the foam be sufficiently stable upon release from its container to allow for adequate coating over the target substrate, while at the same time being able to break readily upon application of shear force such as gentle rubbing. These foaming problems are further exacerbated by the fact that oils themselves are known to collapse foams.

The oil foam compositions of the present invention are typically dispensed from a pressurized canister via a propellant. Expulsion of the canister's content results in the release of the oil foam. The formulation of an oil foam composition which is both physically and chemically stable, can be stored in a pressurized canister with a propellant, satisfactorily disperses the active(s) contained therein and can form an adequately breakable foam upon application of shear, is challenging to say the least.

SUMMARY OF THE INVENTION

The present invention is directed to an anhydrous oil foam composition containing:
(a) at least one liquid oil;
(b) at least one surfactant chosen from polyglyceryl-2 laurate;
(c) at least one UV filter; and
(d) a propellant, wherein the composition is waterless and is capable of imparting UV protection onto a target keratinous substrate.

The present invention is also directed to a method of protecting a keratinous substrate from UV rays involving applying the anhydrous oil foam composition onto the keratinous substrate.

DETAILED DESCRIPTION OF THE INVENTION

Other than in the operating examples, or where otherwise indicated, all numbers expressing quantities of ingredients and/or reaction conditions, are to be understood as being modified in all instances by the term "about".

It has been surprisingly and unexpectedly discovered by the inventors that the use of a certain surfactant in an anhydrous oily foam composition having UV protective properties, yields exceptional chemical and physical foam stability. The oily foam composition, once expelled from its canister via a propellant, possesses sufficient stability to enable it to be effectively spread over a target keratinous substrate surface. The oily foam composition, in the form of an oil mousse, contains: a lipophilic carrier; at least one UV filter; at least one surfactant chosen from a polyglyceryl-2 laurate; and a propellant.

The term "waterless", as used herein, means that the composition contains from 0 up to 5%, preferably less than 3%, most preferably less than 1% by weight of water, based on the total weight of the composition.

The term "keratinous substrate", as used herein, means hair, skin and nails.

Liquid Oil

The at least one liquid oil may be chosen from volatile oils and non-volatile oils.

The composition according to the invention may comprise at least one volatile oil.

For the purposes of the invention, the term "volatile oil" means any oil that is capable of evaporating on contact with the skin, at room temperature and atmospheric pressure. The volatile oils of the invention are volatile cosmetic oils that are liquid at room temperature, with a non-zero vapour pressure at room temperature and atmospheric pressure, ranging in particular from 0.13 Pa to 40 000 Pa (0.001 to 300 mmHg) and preferably ranging from 1.3 Pa to 1300 Pa (0.01 to 10 mmHg).

The volatile oil may be chosen from volatile hydrocarbon-based oils, volatile silicone oils and volatile fluoro oils, and mixtures thereof.

The term "hydrocarbon-based oil" means an oil mainly containing hydrogen and carbon atoms and possibly oxygen, nitrogen, sulfur and/or phosphorus atoms.

The volatile hydrocarbon-based oils may be chosen from hydrocarbon-based oils containing from 8 to 16 carbon atoms, and especially branched $C_8$-$C_{16}$ alkanes, for instance $C_8$-$C_{16}$ isoalkanes of petroleum origin (also known as isoparaffins), for instance isododecane (also known as 2,2,4,4,6-pentamethyl-heptane), isodecane and isohexadecane, for example the oils sold under the trade names Isopar® and Permethyl®.

Volatile oils that may also be used include volatile silicones, for instance volatile linear or cyclic silicone oils, especially those with a viscosity $\leq$5 centistokes ($5 \times 10^{-6}$ m$^2$/s) and especially containing from 2 to 10 silicon atoms and preferably from 2 to 7 silicon atoms, these silicones optionally comprising alkyl or alkoxy groups containing from 1 to 10 carbon atoms. As volatile silicone oils that may be used in the invention, mention may be made especially of octamethyl cyclotetrasiloxane, decamethyl cyclopentasiloxane, dodecamethyl cyclohexasiloxane, heptamethyl hexyltrisiloxane, heptamethyloctyl trisiloxane, hexamethyl disiloxane, octamethyl trisiloxane, decamethyl tetrasiloxane and dodecamethyl pentasiloxane, and mixtures thereof.

Volatile oils that may also be used are volatile fluoro oils: mention may be made of nonafluoroethoxybutane, nonafluoromethoxybutane, decafluoropentane, tetradecafluorohexane and dodecafluoropentane, and mixtures thereof.

The composition according to the invention may comprise at least one non-volatile oil.

The term "non-volatile oil" means an oil that remains on the skin at room temperature and atmospheric pressure for at least several hours and that especially has a vapour pressure of less than 0.13 Pa (0.01 mmHg).

These non-volatile oils may be hydrocarbon-based oils especially of animal or plant origin, or silicone oils, or mixtures thereof. The term "hydrocarbon-based oil" means an oil containing mainly hydrogen and carbon atoms and possibly oxygen, nitrogen, sulfur and/or phosphorus atoms.

The non-volatile oils may be chosen especially from non-volatile hydrocarbon-based oils, which may be fluorinated, and/or non-volatile silicone oils.

Non-volatile hydrocarbon-based oils that may especially be mentioned include:
(a) hydrocarbon-based oils of animal origin;
(b) hydrocarbon-based oils of plant origin, such as triglycerides consisting of fatty acid esters of glycerol, the fatty acids of which may have varied chain lengths from $C_4$ to $C_{24}$, these chains possibly being linear or branched, and saturated or unsaturated; these oils are especially heptanoic or octanoic acid triglycerides, or alternatively wheatgerm oil, sunflower oil, grapeseed oil, sesame seed oil, corn oil, apricot oil, castor oil, shea oil, avocado oil, olive oil, soybean oil, sweet almond oil, palm oil, rapeseed oil, cottonseed oil, hazelnut oil, macadamia oil, jojoba oil, alfalfa oil, poppyseed oil, pumpkin oil, sesame seed oil, marrow oil, rapeseed oil, blackcurrant oil, evening primrose oil, millet oil, barley oil, quinoa oil, rye oil, safflower oil, candlenut oil, passionflower oil or musk rose oil; shea butter; or caprylic/capric acid triglycerides, for instance those sold by the company Stéarineries Dubois or those sold under the names Miglyol 810®, 812® and 818® by the company Dynamit Nobel;
(c) synthetic ethers containing from 10 to 40 carbon atoms;
(d) linear or branched hydrocarbons of mineral or synthetic origin, such as petroleum jelly, polydecenes, hydrogenated polyisobutene such as Parleam®, squalane and liquid paraffins, and mixtures thereof;
(e) synthetic esters, for instance oils of formula $R_1COOR_2$ in which $R_1$ represents a linear or branched fatty acid residue containing from 1 to 40 carbon atoms and $R_2$ represents a hydrocarbon-based chain, which is especially branched, containing from 1 to 40 carbon atoms, on condition that $R_1+R_2 \geqq 10$, for instance purcellin oil (cetostearyl octanoate), isopropyl myristate, isopropyl palmitate, $C_{12}$ to $C_{15}$ alkyl benzoates, hexyl laurate, diisopropyl adipate, isononyl isononanoate, 2-ethylhexyl palmitate, isostearyl isostearate, 2-hexyldecyl laurate, 2-octyldecyl palmitate, 2-octyldodecyl myristate, or alcohol or polyalcohol heptanoates, octanoates, decanoates or ricinoleates, for instance propylene glycol dioctanoate; hydroxylated esters, for instance isostearyl lactate, diisostearyl malate or 2-octyldodecyl lactate; polyol esters and pentaerythritol esters;
(f) fatty alcohols that are liquid at room temperature with a branched and/or unsaturated carbon-based chain containing from 12 to 26 carbon atoms, for instance octyldodecanol, isostearyl alcohol, oleyl alcohol, 2-hexyldecanol, 2-butyloctanol or 2-undecylpentadecanol, and
(g) higher fatty acids such as oleic acid, linoleic acid or linolenic acid, and mixtures thereof.

The non-volatile silicone oils that may be used in the composition according to the invention may be non-volatile polydimethylsiloxanes (PDMS), polydimethylsiloxanes comprising alkyl or alkoxy groups, which are pendent and/or at the end of a silicone chain, these groups each contain from 2 to 24 carbon atoms, phenyl silicones, for instance phenyl trimethicones, phenyl dimethicones, phenyltrimethyl-siloxydiphenylsiloxanes, diphenyl dimethicones and diphenyl-methyldiphenyltrisiloxanes, and mixtures thereof.

The liquid oil is typically present in the composition in an amount of from about 10 to about 90% by weight, preferably from about 30% to about 70% by weight, and more preferably from about 50 to about 65% by weight, based on the total weight of the composition.
Surfactant It has surprisingly and unexpectedly been discovered that the use, in particular, of at least one surfactant chosen from polyglyceryl-2 laurate, facilitates the formation of stable foams created from oils using a propellant, from both a chemical and physical perspective. More particularly, the use of such a surfactant enables the creation of foam capable of carrying sunscreen active ingredients which are homogeneously and finely dispersed therein, wherein the foam is sufficiently stable (i.e. does not collapse prematurely) after being dispensed from its receptacle such that it allows for successful application/coverage over the target keratinous substrate.

At least one surfactant chosen from polyglycerol-2 laurate will typically be present in the composition in an amount of from about 0.1 to about 15% by weight, preferably from about 1 to about 10% by weight, and more preferably from about 3 to about 7% by weight, based on the total weight of the composition.
UV Filters Avobenzone: (trade names are Parsol 1789, Eusolex 9020, Escalol 517 and others, INCI Butyl Methoxydibenzoylmethane). It is a dibenzoylmethane derivative.

Octinoxate: Octyl methoxycinnamate (INCI) or octinoxate (USAN), trade names Eusolex 2292, Parsol MCX, Uvinul MC80.

Examples of suitable sunscreen actives which may be used in the present invention include, but are not limited to, dibenzoylmethane derivatives such as butyl methoxydibenzoylmethane, also known as avobenzone, and commercially available under the tradenames Parsol® 1789, Eusolex® 9020, and Escalol® 517; octyl methoxycinnamate commercially available under the tradenames Eusolex® 2292, Parsol® MCX, and Univul® MC80; anthranilates; salicylic derivatives; camphor derivatives; benzophenone derivatives; β,β-diphenylacrylate derivatives; triazine derivatives; benzotriazole derivatives; benzalmalonate derivatives; benzimidazole derivatives; imidazolines; bis-benzazolyl derivatives as described in patents EP 669 323 and U.S. Pat. No. 2,463,264; p-aminobenzoic acid (PABA) derivatives; methylenebis(hydroxyphenylbenzotriazole) derivatives as described in patent applications U.S. Pat. No. 5,237,071, U.S. Pat. No. 5,166,355, GB 2 303 549, DE 197 26 184 and EP 893 119; benzoxazole derivatives such as those described in patent applications EP 0 832 642; EP 1 027 883, EP 1 300 137 and DE 101 62 844; screening polymers and screening silicones such as those described especially in patent application WO 93/04665; dimers derived from α-alkylstyrene, such as those described in patent application DE 198 55 649; 4,4-diarylbutadienes such as those described in patent applications EP 0 967 200, DE 197 46 654, DE 197 55 649, EP-A-1 008 586, EP 1 133 980 and EP 133 981, and mixtures thereof.

As examples of organic photoprotective agents, mention may be made of those denoted hereinbelow under their INCI name:
 para-Aminobenzoic acid derivatives:
 PABA,
 Ethyl PABA,
 Ethyl dihydroxypropyl PABA,
 Ethylhexyl dimethyl PABA sold in particular under the name "Escalol 507" by ISP,
 Glyceryl PABA,
 PEG-25 PABA sold under the name "Uvinul P25" by BASF.
 Salicylic Derivatives:
 Homosalate sold under the name "Eusolex HMS" by Rona/EM Industries,
 Ethylhexyl salicylate sold under the name "Neo Heliopan OS" by Haarmann and Reimer, Dipropylene glycol salicylate sold under the name "Dipsal" by Scher, TEA salicylate sold under the name "Neo Heliopan TS" by Haarmann and Reimer.

β,β-Diphenylacrylate derivatives:

Octocrylene sold in particular under the trade name "Uvinul N539" by BASF,

Etocrylene sold in particular under the trade name "Uvinul N35" by BASF.

Benzophenone Derivatives:

Benzophenone-1 sold under the trade name "Uvinul 400" by BASF,

Benzophenone-2 sold under the trade name "Uvinul D50" by BASF,

Benzophenone-3 or Oxybenzone sold under the trade name "Uvinul M40" by BASF,

Benzophenone-4 sold under the trade name "Uvinul MS40" by BASF,

Benzophenone-5,

Benzophenone-6 sold under the trade name "Helisorb 11" by Norquay,

Benzophenone-8 sold under the trade name "Spectra-Sorb UV-24" by American Cyanamid, Benzophenone-9 sold under the trade name "Uvinul DS-49" by BASF, Benzophenone-12

Diethylaminohydroxybenzoylhexyl benzoate sold under the trade name "Uvinul A Plus" by BASF, Benzylidenecamphor Derivatives:

3-Benzylidenecamphor manufactured under the name "Mexoryl SD" by Chimex,

4-Methylbenzylidenecamphor sold under the name "Eusolex 6300" by Merck,

Benzylidenecamphorsulfonic acid manufactured under the name "Mexoryl SL" by Chimex, Camphor benzalkonium methosulfate manufactured under the name "Mexoryl SO" by Chimex, Terephthalylidenedicamphorsulfonic acid manufactured under the name "Mexoryl SX" by Chimex, Polyacrylamidomethylbenzylidenecamphor manufactured under the name "Mexoryl SW" by Chimex.

Phenylbenzimidazole Derivatives:

Phenylbenzimidazolesulfonic acid sold in particular under the trade name "Eusolex 232" by Merck, Disodium phenyl dibenzimidazole tetrasulfonate sold under the trade name "Neo Heliopan AP" by Haarmann and Reimer.

Phenylbenzotriazole Derivatives:

Drometrizole trisiloxane sold under the name "Silatrizole" by Rhodia Chimie,

Methylenebis(benzotriazolyl)tetramethylbutylphenol sold in solid form under the trade name "MIXXIM BB/100" by Fairmount Chemical, or in micronized form as an aqueous dispersion under the trade name "Tinosorb M" by Ciba Specialty Chemicals.

Triazine Derivatives:

-Bis(ethylhexyloxyphenol)methoxyphenyl triazine sold under the trade name "Tinosorb S" by Ciba-Geigy, Ethylhexyltriazone sold in particular under the trade name "Uvinul T150" by BASF, Diethylhexylbutamidotriazone sold under the trade name "Uvasorb HEB" by Sigma 3V, 2,4,6-tris(diisobutyl 4'-aminobenzalmalonate)-s-triazine.

Anthranilic derivatives:

Menthyl anthranilate sold under the trade name "Neo Heliopan MA" by Haarmann and Reimer.

Imidazoline Derivatives:

Ethylhexyldimethoxybenzylidenedioxoimidazoline propionate.

Benzalmalonate Derivatives:

Polyorganosiloxane containing benzalmalonate functions, for instance Polysilicone-15, sold under the trade name "Parsol SLX" by Hoffmann LaRoche 4,4-Diarylbutadiene Derivatives:

1,1-Dicarboxy(2,2'-dimethylpropyl)-4,4-diphenyl-butadiene

Benzoxazole derivatives:

2,4-bis[5-(1-dimethylpropyl)benzoxazol-2-yl(4-phenyl)imino]-6-(2-ethylhexyl)imino-1,3,5-triazine sold under the name Uvasorb K2A by Sigma 3V and mixtures thereof.

Examples of mineral photoprotective agents are chosen from pigments and even more preferably nanopigments (mean size of the primary particles: generally between 5 nm and 100 nm and preferably between 10 nm and 50 nm) of treated or untreated metal oxides such as, for example, nanopigments of titanium oxide (amorphous or crystallized in rutile and/or anatase form), of iron oxide, of zinc oxide, of zirconium oxide or of cerium oxide.

The treated nanopigments are pigments that have undergone one or more surface treatments of chemical, electronic, mechanochemical and/or mechanical nature with compounds as described, for example, in Cosmetics & Toiletries, February 1990, Vol. 105, pp. 53-64, such as amino acids, beeswax, fatty acids, fatty alcohols, anionic surfactants, lecithins, sodium, potassium, zinc, iron or aluminium salts of fatty acids, metal (titanium or aluminium) alkoxides, poly-ethylene, silicones, proteins (collagen or elastin), alkanolamines, silicon oxides, metal oxides, sodium hexametaphosphate, alumina or glycerol.

The treated nanopigments may more particularly be titanium oxides treated with:

(a) silica and alumina, such as the products "Micro-titanium Dioxide MT 500 SA" and "Microtitanium Dioxide MT 100 SA" from the company Tayca, and the products—sold under the tradename "Solaveil® XT-100", "Solaveil® XT-300", "Solaveil® XT-40W", "Tioveil® 50 FCM" "Tioveil® 50 Fin", and "Solaveil® Clarus" from the company Croda-alumina and aluminium stearate, such as the product "Microtitanium Dioxide MT 100 T" from the company Tayca, (b) alumina and aluminium laurate, such as the product "Microtitanium Dioxide MT 100 S" from the company Tayca, (c) iron oxides and iron stearate, such as the product "Microtitanium Dioxide MT 100 F" from the company Tayca, (d) silica, alumina and silicone, such as the products "Microtitanium Dioxide MT 100 SAS", "Microtitanium Dioxide MT 600 SAS" and "Microtitanium Dioxide MT 500 SAS" from the company Tayca, (e) sodium hexametaphosphate, such as the product "Microtitanium Dioxide MT 150 W" from the company Tayca, (f) octyltrimethoxysilane, such as the product "T-805" from the company Degussa, (g) alumina and stearic acid, such as the product "UVT-M160" from the company Kemira, (h) alumina and glycerol, such as the product "UVT-M212" from the company Kemira, (i) alumina and silicone, such as the product "UVT-M262" from the company Kemira.

Other titanium oxide nanopigments treated with a silicone are preferably $TiO_2$ treated with octyltrimethylsilane and for which the mean size of the elementary particles is between 25 and 40 nm, such as the product sold under the trade name "T805" by the company Degussa Silices, $TiO_2$ treated with a polydimethylsiloxane and for which the mean size of the elementary particles is 21 nm, such as the product sold under the trade name "70250 Cardre UF TiO2SI3" by the company Cardre, anatase/rutile $TiO_2$ treated with a polydimethylhydrogenosiloxane and for which the mean size of the elementary particles is 25 nm, such as the product sold under the trade name "Microtitanium Dioxide USP Grade Hydrophobic" by the company Color Techniques.

The uncoated titanium oxide nanopigments are sold, for example, by the company Tayca under the trade names "Microtitanium Dioxide MT 500 B" or "Microtitanium Dioxide MT 600 B", by the company Degussa under the name "P 25", by the company Wackher under the name "Oxyde de titane transparent PW", by the company Myoshi Kasei under the name "UFTR", by the company Tomen under the name "ITS" and by the company Tioxide under the name "Tioveil AQ".

The uncoated zinc oxide nanopigments are, for example:
(a) those sold under the name "Z-Cote®" by the company Sunsmart;
(b) those sold under the name "Nanox®" by the company Element is;
(c) those sold under the name "Nanogard® WCD 2025" by the company Nanophase Technologies.

The coated zinc oxide nanopigments are, for example:
(d) those sold under the name "Zinc Oxide CS-5®" by the company Toshibi (ZnO coated with polymethylhydrogenosiloxane);
(e) those sold under the name "Nanogard Zinc Oxide FN®" by the company Nanophase Technologies (as a 40% dispersion in Finsolv TN, $C_{12}$-$C_{15}$ alkyl benzoate);
(f) those sold under the name "Daitopersion® ZN-30" and "Daitopersion® ZN-50" by the company Daito (dispersions in cyclopolymethylsiloxane/oxyethylenated polydimethyl-siloxane, containing 30% or 50% of nanozinc oxides coated with silica and polymethylhydrogenosiloxane);
(g) those sold under the name "NFD Ultrafine ZNO®" by the company Daikin (ZnO coated with perfluoroalkyl phosphate and copolymer based on perfluoroalkylethyl as a dispersion in cyclopentasiloxane);
(h) those sold under the name "SPD-Z1®" by the company Shin-Etsu (ZnO coated with silicone-grafted acrylic polymer, dispersed in cyclodimethylsiloxane);
(i) those sold under the name "Escalol Z100®" by the company ISP (alumina-treated ZnO dispersed in an ethylhexyl methoxycinnamate/PVP-hexadecene/methicone copolymer mixture);
(j) those sold under the name "Fuji ZNO-SMS-10®" by the company Fuji Pigment (ZnO coated with silica and polymethylsilsesquioxane);
(k) those sold under the name "Nanox Gel TN®" by the company Elementis (ZnO dispersed at a concentration of 55% in $C_{12}$-$C_{15}$ alkyl benzoate with hydroxystearic acid polycondensate).

The uncoated cerium oxide nanopigments are sold under the name "Colloidal Cerium Oxide®" by the company Rhone-Poulenc.

The uncoated iron oxide nanopigments are sold, for example, by the company Arnaud under the names "Nanogard® WCD 2002 (FE 45B)", "Nanogard® Iron FE 45 BL AQ", "Nanogard® FE 45R AQ" and "Nanogard® WCD 2006 (FE 45R)" or by the company Mitsubishi under the name "TY-220", The coated iron oxide nanopigments are sold, for example, by the company Arnaud under the names "Nanogard® WCD 2008 (FE 45B FN)", "Nanogard® WCD 2009 (FE 45B 556)", "Nanogard® FE 45 BL 345" and "Nanogard® FE 45 BL" or by the company BASF under the name "Transparent Iron Oxide®".

Mention may also be made of mixtures of metal oxides, especially of titanium dioxide and of cerium dioxide, including the silica-coated equal-weight mixture of titanium dioxide and of cerium dioxide, sold by the company Ikeda under the name "Sunveil® A", and also the alumina, silica and silicone-coated mixture of titanium dioxide and of zinc dioxide, such as the product "M 261" sold by the company Kemira, or the alumina, silica and glycerol-coated mixture of titanium dioxide and of zinc dioxide, such as the product "M 211" sold by the company Kemira.

The nanopigments may be introduced into the compositions according to the invention in unmodified form or in the form of pigmentary paste, i.e. as a mixture with a dispersant, as described, for example, in document GB-A-2 206 339.

The at least one sunscreen active is typically present in an amount of from about 0.1 to about 50% by weight, such as from about 5 to about 50% by weight, and from about 9 to about 30% by weight, based on the total weight of the composition.

It has also been unexpectedly discovered that the anhydrous foam generated by the present invention is capable of carrying large quantities of sunscreen active, i.e. greater than 35% by weight, based on the total weight of the composition, while at the same time remaining chemically and physically stable upon emission from its receptacle. This phenomenon is critical when formulating anhydrous oil mousse products having high SPF values.

Propellants

Suitable propellants for use in the present invention include volatile liquefied propellant gases such as, for example, dimethyl ether (DME) and/or linear or branched-chain hydrocarbons with two to five carbon atoms such as, for example, ethane, propane, butane, isobutene and pentane, which can be used alone or in admixture with each other.

Compressed air, as well as other pressurized gases suitable for cosmetic use may also be employed. Examples thereof include, but are not limited to, air, oxygen, nitrogen, hydrogen, helium, krypton, xenon, radon, argon, nitrous oxide and carbon dioxide.

Auxiliaries

The composition according to the invention may comprise at least one dyestuff chosen especially from pigments, nacres, liposoluble dyes and water-soluble dyes, and mixtures thereof.

The term "pigments" should be understood as meaning white or coloured, mineral or organic particles of any shape, which are insoluble in the physiological medium and are intended to colour the composition.

The term "nacres" should be understood as meaning iridescent particles of any shape, especially produced by certain molluscs in their shell or else synthesized.

The term "dyes" should be understood as meaning generally organic compounds that are soluble in water or in fatty substances such as oils.

The pigments may be white or coloured, and mineral and/or organic. Among the mineral pigments that may be mentioned are titanium dioxides, optionally surface-treated, zirconium oxide and cerium oxide, and also zinc oxide, iron oxide (black, yellow or red) or chromium oxide, manganese violet, ultramarine blue, chromium hydrate and ferric blue and metal powders such as aluminium powder or copper powder.

An example that may be mentioned is micronized titanium dioxide powder surface-treated with a silica/aluminium hydroxide/alginic acid mixture, sold under the name MT-100AQ.

Among the organic pigments that may be mentioned are carbon black, pigments of D&C type and lakes based on cochineal carmine or on barium, strontium, calcium or aluminium.

The nacreous pigments may be chosen from white nacreous pigments such as mica coated with titanium or with bismuth oxychloride, coloured nacreous pigments such as titanium mica coated with iron oxides, titanium mica coated especially with ferric blue or with chromium oxide, titanium mica coated with an organic pigment of the abovementioned type, and also nacreous pigments based on bismuth oxychloride.

The liposoluble dyes are, for example, Sudan red, D&C Red No 17, D&C Green No 6, β-carotene, soybean oil, Sudan brown, D&C Yellow No 11, D&C Violet No 2, D&C Orange No 5, quinoline yellow, annatto and bromo acids.

The dyestuffs may be present in an amount of from about 0.01% to about 30% by weight, such as from about 0.1% to about 20% by weight, such as from about 0.5% to about 15% by weight, and most preferably from about 0.5% to about 5% by weight, relative to the total weight of the composition.

In a known manner, the composition of the invention may also contain adjuvants that are common in cosmetics, such as humectants, preserving agents, antioxidants, complexing agents, solvents, fragrances, bactericides, odour absorbers, vitamins, moisturizers, self-tanning compounds and anti-wrinkle active agents. The amounts of these various adjuvants are those conventionally used in the field under consideration, for example from 0.01% to 20% of the total weight of the composition. Depending on their nature, these adjuvants may be introduced into the fatty phase, into the aqueous phase and/or into lipid vesicles.

Needless to say, a person skilled in the art will take care to select this or of these optional additional compound(s), and/or the amount thereof, such that the advantageous properties of the composition according to the invention are not, or are not substantially, adversely affected by the envisaged addition.

The composition in the foam form according to the invention finds its application in a wide variety of treatments, especially cosmetic treatments, of the skin, the lips and the hair, including the scalp, especially for treating, protecting or caring for the skin, the lips and/or the hair, and/or for making up the skin and/or the lips. It may also be intended for treating dry skin and/or dry lips, while at the same time delivering adequate SPF protection.

Thus, a subject of the invention is also the cosmetic use of the composition in the foam form as defined above for treating, or caring for the skin, the lips and/or the hair, and/or for making up the skin and/or the lips, while at the same time protecting these keratinous substrates from harmful UV rays.

The composition before expansion in volume can be provided in the suspension, dispersion, solution or gel form.

In order for the foam to be of acceptable quality, both aesthetically and from an application point of view, the foam should possess a density of from about 0.03 to about 0.15 g/ml, preferably from about 0.04 to about 0.08 g/ml, and more preferably from about 0.04 to about 0.06 g/ml.

Preparation Process

The composition in the foam form may be obtained from a base composition in a distributor. This distributor may be an aerosol containing, besides the base composition, a propellant.

This propellant may represent less than 20% by weight of the base composition and in particular may represent from 1% to 10% by weight, for example from 2 to 8% by weight, for example at least 5% by weight of the total weight of the base composition. The propellant that may be used may be chosen from carbon dioxide, nitrogen, nitrous oxide and volatile hydrocarbons such as butane, isobutane, propane, ethane, pentane, isododecane or isohexadecane, and mixtures thereof.

It may especially be a propane/butane mixture (Liquified Petroleum Gas or LPG) in a weight ratio [propane/butane] ranging from 0.1 to 1, especially of 0.31.

The pressure of the propellant, and for example of said propane/butane mixture, in the aerosol may range from 0.20 to 0.50 MPa, for example from 0.20 to 0.40, and especially from 0.25 to 0.35 MPa.

The compositions employed in the invention can be prepared by processes for mixing, stirring or dispersing compressed gases, such as air, chlorofluorocarbon-based compounds, nitrogen, carbon dioxide, oxygen or helium, a process for mixing and stirring in the presence of a foaming agent, such as a surfactant.

In particular, the composition is prepared by mixing the ingredients with stirring, generally under hot conditions, and by then expanding in volume under the action of a gas, it being possible for the gas to be introduced during the stage of cooling the composition or after preparation of the composition, for example using a device for expanding in volume of Mondomix type, a beater of Kenwood type, a scraped-surface exchanger or a dynamic mixer (of IMT type, for example). The gas is preferably air or nitrogen.

The composition according to the invention can be packaged in a container delimiting at least one compartment which comprises the composition, the container being closed by a closure part. The container can be equipped with a means for the dispensing of the product. In particular, the container can be equipped with a pump.

The composition can be applied, e.g., by finger or using an applicator.

The container is preferably used in combination with an applicator comprising at least one application component configured in order to apply the composition to keratinous substances.

According to another advantageous embodiment, the applicator comprises an application nozzle.

EXAMPLES

The examples which follow are presented by way of illustration and without limitation of the invention. Unless otherwise indicated, the amounts are given as percent by weight.

Example 1

1 Various formulations were prepared, each containing 95% oil and 5% surfactant.
2 These formulations were then introduced into aerosol packages.
3 LPG (Liquefied petroleum gas) consisting of isobutane and propane was then introduced into the aerosol packages.

4 Foam was dispensed from the packages and then measured to determine its foam density.

5 Visual observations were then made to ascertain the quality of the dispensed and foam.

Foam density was measured by dispensing the foam into a 100 ml jar, measuring its weight, and then calculating its foam density in g/ml. Foam quality was judged to be good if the foam was sufficiently stable to enable the foam to be properly spread over the target substrate, i.e. foam lasted long enough to be spread over the target surface and then disintegrated immediately after the spreading process, properties that are dependent upon foam density.

| Examples | % Oil | INCI name | Foam density (g/ml) | Result |
|---|---|---|---|---|
| Example 1 | 95% | 5% POLYGLYCERYL-2 LAURATE | 0.0479 | Good foam |
| Comparison example 1 | 95% | 5% POLYGLYCERYL-5 TRIOLEATE | 0.0790 | Poor foam |
| Comparison example 2 | 95% | 5% PEG-12 Dimethicone | N/A | No foam |
| Comparison example 3 | 95% | 5% POLYGLYCERYL-5 LAURATE | 0.1364 | Poor foam |
| Comparison example 4 | 95% | 5% POLYGLYCERYL-10 LAURATE | N/A | No foam |

| Example 2 | |
|---|---|
| INCI US | % in formula |
| OIL | 54.00 |
| PROPELLANT | 10.00 |
| UV FILTERS | 31.50 |
| POLYGLYCERYL-2 LAURATE | 4.50 |

Foam density of Example 2 was determined to be 0.0511 (g/ml) and foam quality was determined to be good.

What is claimed is:

1. A method of protecting a keratinous substrate from UV rays comprising applying onto the keratinous substrate an anhydrous oil foam composition containing:
   (a) at least one liquid oil;
   (b) at least one surfactant chosen from polyglyceryl-2 laurate;
   (c) at least one UV filter; and
   (d) a propellant,
   wherein the composition is waterless and is capable of imparting UV protection onto a target keratinous substrate;
   wherein (a) is chosen from Natural oils, Ester oils, Mineral oils; and
   wherein (a) is present in the composition in an amount of from about 30 to about 70% by weight, based on the weight of the composition.

2. The method of claim 1 wherein (a) is present in the composition in an amount of from about 50 to about 65% by weight, based on the weight of the composition.

3. The method of claim 1 wherein (b) is present in the composition in an amount of from about 0.1 to about 15% by weight, based on the weight of the composition.

4. The method of claim 1 wherein (b) is present in the composition in an amount of from about 3 to about 7% by weight, based on the weight of the composition.

5. The method of claim 1 wherein (c) is present in the composition in an amount of from about 0.1 to about 50% by weight, based on the weight of the composition.

6. The method of claim 1 wherein (c) is present in the composition in an amount of from about 9 to about 30% by weight, based on the weight of the composition.

7. The method of claim 1 wherein the composition further comprises at least one dyestuff.

8. The method of claim 1 wherein the composition produces foam having a foam density of from about 0.03 to about 0.15 g/ml.

9. The method of claim 1 wherein the composition produces foam having a foam density of from about 0.04 to about 0.06 g/ml.

* * * * *